United States Patent
Seizew et al.

(10) Patent No.: US 6,696,297 B2
(45) Date of Patent: Feb. 24, 2004

(54) NON-OXIDIZABLE BILIRUBIN SUBSTITUTES AND USES THEREFOR

(75) Inventors: Alex Michael Seizew, Oxnard, CA (US); Sean Michael Teel, Agoura, CA (US)

(73) Assignee: Medical Analysis Systems, Inc., Camarillo, CA (US)

(*) Notice: Subject to any disclaimer, the term of this patent is extended or adjusted under 35 U.S.C. 154(b) by 421 days.

(21) Appl. No.: 09/782,478

(22) Filed: Feb. 13, 2001

(65) Prior Publication Data

US 2002/0146630 A1 Oct. 10, 2002

(51) Int. Cl.$^7$ .................. G01N 31/00; G01N 33/72
(52) U.S. Cl. .................. 436/12; 436/8; 436/97; 436/164; 436/166; 252/408.1
(58) Field of Search .................. 436/8, 12, 97, 436/164, 166, 171; 252/408.1

(56) References Cited

U.S. PATENT DOCUMENTS

| | | | | |
|---|---|---|---|---|
| 4,344,864 A | * | 8/1982 | Louderback et al. | 436/12 |
| 5,278,073 A | * | 1/1994 | Grandjean | 436/12 |
| 5,281,536 A | * | 1/1994 | Wild et al. | 436/16 |
| 5,854,073 A | * | 12/1998 | Burns et al. | 436/12 |
| 5,935,861 A | * | 8/1999 | Gnezda et al. | 436/97 |

FOREIGN PATENT DOCUMENTS

JP        6-294799      * 10/1994

OTHER PUBLICATIONS

Xie et al. Tetrahedron, vol. 49, No. 11, pp. 2185–2200, 1993.*
Kar et al. Tetrahedron, vol. 54, pp. 5151–5170, 1998.*
Hwang et al. Tetrahedron, vol. 50, No. 33, pp. 9919–9932, 1994.*
Kar et al. Tetrahedron, vol. 54, pp. 12671–12690, 1998.*

* cited by examiner

Primary Examiner—Maureen M. Wallenhorst
(74) Attorney, Agent, or Firm—Christie, Parker & Hale, LLP

(57) ABSTRACT

Compositions and methods are disclosed for use in the analysis and quantitation of conjugated and unconjugated bilirubin in patient or other samples. The compositions have the general formula:

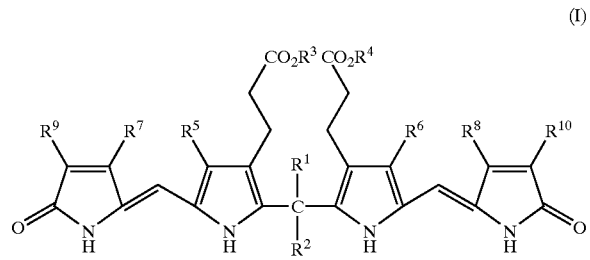

(I)

wherein:
$R^1$ and $R^2$ are independently selected from alkyl and aryl,
$R^3$ and $R^4$ are independently selected from hydrogen, alkyl, alkenyl, tauryl, aryl, and glucoronyl, and
$R^5$, $R^6$, $R^7$, $R^8$, $R^9$ and $R^{10}$ are each independently selected from hydrogen and alkyl, and are resistant to oxidation, as occurs in bilirubin upon exposure to light and air. These properties make them ideal for use in calibration and control solutions for use in medical and research bilirubin analysis, or other applications where stable reagents for bilirubin analysis is desirable.

36 Claims, No Drawings

NON-OXIDIZABLE BILIRUBIN SUBSTITUTES AND USES THEREFOR

BACKGROUND OF THE INVENTION

The field of the invention is stable liquid control and/or calibration compositions for use in clinical diagnostic applications, particularly those used to quantitate bilirubin.

Bilirubin is a yellow-orange bile pigment primarily resulting from the degradation of heme from hemoglobin in red blood cells. The average human produces 250 to 300 mg bilirubin each day, which is transported to the liver in association with albumin. Inside the liver, bilirubin is conjugated with glucuronic acid to produce bilirubin mono- and diglucuronide, (collectively referred to as direct bilirubin) which is excreted into bile.

The concentration of bilirubin in the blood increases in response to increases in the amount of hemoglobin degraded, as well as a decrease in liver function. There are several inherited and acquired diseases which affect steps in the production, uptake, storage, metabolism and excretion of bilirubin, including physiological jaundice, Crigler-Najjar syndromes Types I and II, Gilbert's syndrome and the Dubin-Johnson syndrome. The disturbances of bilirubin metabolism associated with physiological jaundice and Crigler-Najjar syndromes Types I and II result in elevated unconjugated bilirubin levels in serum. On the other hand, total serum bilirubin levels decrease as a result of bilirubin metabolism disturbances associated with Gilbert's syndrome and the Dubin-Johnson syndrome. Therefore, quantification of the amount of bilirubin in biological fluids is a crucial clinical tool to diagnose and regulate disease.

There are commercially available calibration and control products. The most common is lyophilized serum which contains natural bilirubin. An example is LYPHOCHEK (Bio-Rad Laboratories). Lyophilized controls suffer from disadvantages in that errors can be made in reconstitution (e.g., incorrect amounts of water added, or incomplete resuspension of all lyophilized product) and they have a relatively short life due to oxidation of bilirubin when reconstituted, making them potentially wasteful and expensive to use.

Liquid controls and calibrators are also available, such as CHEMTRAK™, a liquid bilirubin control and calibration solution (Medical Analysis Systems, Inc.), and LIQ-UICHEK™ (Bio-Rad Laboratories). These controls have the advantage of being in liquid form and having up to an 18-month shelf life at 2 to 8° C. if unopened (CHEMTRAK™). However, once opened, such solutions have a 14-day stability if used as a control solution and a 7-day stability if used as a calibration solution, again due at least in part to the oxidation of bilirubin to biliverdin.

Accordingly, it is evident that a need exists for an improved, more stabile, bilirubin standard.

SUMMARY OF THE INVENTION

The present invention uses C10 substituted synthetic bilirubin analogs in calibration and control compositions which are stable against oxidation for periods of months to years when unopened, and weeks to months, or longer, when opened and exposed to oxidizing conditions. Compositions of the formula:

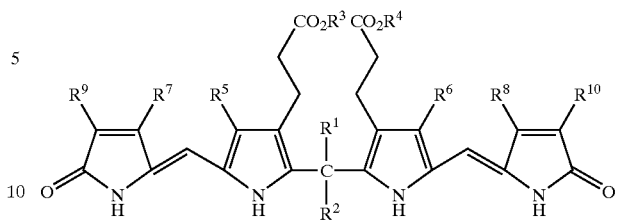

wherein:
$R^1$ and $R^2$ are each independently selected from alkyl, alkenyl, alkynyl, heterocyclic, and aryl;
$R^3$ and $R^4$ are each independently selected from hydrogen, alkyl, alkenyl, glucoronyl, tauryl, and aryl; and
$R^5$, $R^6$, $R^7$, $R^8$, $R^9$ and $R^{10}$ are each independently selected from hydrogen, alkyl, and alkenyl are extremely resistant to oxidation, yet are reactive with diazo compounds commonly used in the analysis and quantification of bilirubin and unrobilinogen for clinical and research purposes. While the disclosure generally refers to detection and analysis of bilrubin, it is understood that it can apply equally well to the detection and analysis of unbilinogen.

The invention features a method of quantifying bilirubin in a sample comprising detecting bilirubin in a sample to obtain a measurement indicative of the amount of bilirubin in the sample, detecting a known quality of a compound of Formula (I) above in at least one control reagent to obtain a measurement indicative of the amount of the compound in the control reagent, and comparing the measurements to determine the amount of bilirubin in the sample compared to the amount of the compound of Formula (I) in the control reagent. In a preferred embodiment, the detection is done by measuring a diazotization reaction involving contacting the bilirubin in the sample and the compound in the control reagent with a diazonium ion source to form colored products which are measured, e.g., spectrophotometrically. This method has the advantage that it can be used in many currently available clinical analysis platforms.

The invention also features a method of calibrating a device to accurately detect bilirubin comprising detecting with the device a known quantity of a compound of Formula (I) in at least one calibration reagent to obtain a measurement indicative of the amount of the compound in the calibration reagent, and adjusting the device such that the measurement from the device is the same as or proportional to the known amount of compound in the calibration reagent. In a preferred embodiment, the detection involves measuring the products of a diazotization reaction. The diazotization reaction involves contacting the bilirubin in the sample and the compound in the control reagent with a diazonium ion source to form colored products, which are measured, e.g., spectrophotometrically. Two or more calibration or control reagents having different amounts of the bilirubin analog compounds of Formula (I) can be used to generate a standard curve, by, for example, creating measurements at the high, low, and/or intermediate ranges where sample concentrations of bilirubin are expected to fall.

Preferably, compounds used in the above methods are those where $R^1$ and $R^2$ are each independently selected from alkyl, alkenyl, alkynyl, heterocyclic, and aryl; $R^3$ and $R^4$ are each independently selected from hydrogen, alkyl, alkenyl, and glucoronyl; and $R^5$, $R^6$, $R^7$, $R^8$, $R^9$ and $R^{10}$ are each independently selected from hydrogen and alkyl. Particularly preferred compounds are those where $R^1$ and $R^2$ are methyl; and/or where $R^3$ and $R^4$ are each hydrogen. Preferably, the calibration and control reagents are provided as a liquid, but they can also be supplied in any other form, e.g., as a lyophilized powder.

The invention also features compositions for use in calibration or control solutions. These compositions comprise a synthetic bilirubin analog of Formula (I):

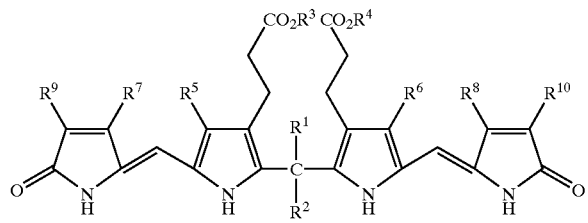

(I)

wherein
$R^1$ and $R^2$ are independently selected from alkyl, alkenyl, alkynyl, heterocyclic, and aryl;
$R^3$ and $R^4$ are indenpendently selected from hydrogen, alkyl, alkenyl, glucoronyl, tauryl, and aryl; and
$R^5$, $R^6$, $R^7$, $R^8$, $R^9$ and $R^{10}$ are each independently selected from hydrogen, alkyl, and alkenyl, with the proviso that when $R^3$ and $R^4$ are both hydrogen, at least one of $R^5$, $R^6$, $R^7$, $R^8$, $R^9$ and $R^{10}$ is not alkyl, preferably not alkyl or alkenyl.

Compositions containing the compound of Formula (I) can be provided in any form, but are preferably supplied in liquid form and contain processed serum, urine, or other biological or biologically compatible components. For example, the controls and calibrators can be supplied in any fluid or reconstitute from water or saline to a complex urine or serum matrix. The compositions can also contain preservatives, antibiotics, and/or other analytes, such as therapeutic drugs, drugs of abuse, biological enzymes, toxins, and metabolites.

Preferred compositions for use as calibration or control reagents include stable bilirubin analogs of Formula (I) wherein $R^1$ and $R^2$ are methyl, $R^3$ and $R^4$ are selected independently from the group containing hydrogen, alkyl, alkenyl, tauryl, aryl, and glucoronyl, and $R^5$, $R^6$, $R^7$, $R^8$, $R^9$ and $R^{10}$ are each independently selected from hydrogen and alkyl; and an additional component selected from processed serum and processed urine. The compositions are preferably provided in a liquid form, but can be lyophilized, and preferably contain at least one of following: preservatives, antibiotics, and/or other analytes, such as therapeutic drugs, drugs of abuse, biological enzymes, toxins, and metabolites. Preferably, $R^7$, $R^8$, $R^9$ and $R^{10}$ are each ethyl.

Other preferred compositions include stable bilirubin analogs of Formula (III):

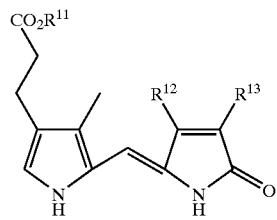

(III)

wherein
$R^{11}$ is selected from the group containing hydrogen, alkyl, tauryl, aryl, and glucoronyl; and $R^{12}$ and $R^{13}$ are independently selected from hydrogen and alkyl, and one of processed serum and processed urine.

DETAILED DESCRIPTION OF THE INVENTION

It has been discovered that certain synthetic bilirubin analogs with geminal substitutions at the C10 position are not readily susceptible to oxidation, making them extremely light-, temperature-, and water-stable as compared to bilirubin. These compounds are nonetheless reactive with diazo compounds. These features make them excellent analytes in clinical and research solutions used, e.g., as controls for patient samples or calibrators for analytical instruments, because of their long shelf life even after opening and less stringent storage requirements. Bilirubin analogs of the invention have the following general formula:

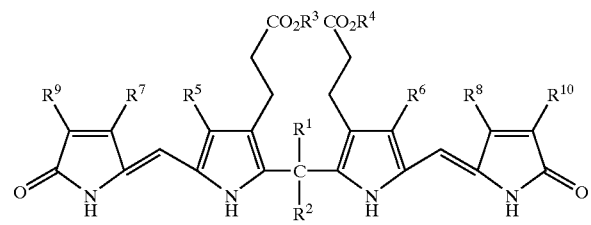

(I)

wherein
$R^1$ and $R^2$ are each independently selected from alkyl, alkenyl, alkynyl, heterocyclic, and aryl;
$R^3$ and $R^4$ are each independently selected from hydrogen, alkyl, tauryl, aryl, and glucoronyl; and
$R^5$, $R^6$, $R^7$, $R^8$, $R^9$ and $R^{10}$ are independently selected from hydrogen, alkyl, and alkenyl.

As used herein, the term "alkyl," alone or in combination, means a straight-chain, branched-chain, or cyclic hydrocarbon, either saturated or unsaturated, optionally substituted, containing from 1 to about 12 carbon atoms. Preferably, alkyls of the invention are methyl, ethyl, propyl, allyl, butyl, pentyl, hexyl, or isomers thereof. Suitable substituents include hydroxy, alkoxy, cycloallyl, aryl, heterocycloallyl, heteroaryl, thio, thioalkyl, fluro, chloro, bromo, iodo, carboxy, carboxyalkyl, carbamoyl, carbamide, amino, amidino, phosphate, phosphonate, phosphinate, phosphinyl, their derivatives, and the like.

As used herein, the term, "alkenyl," alone or in combination, means a straight chain, branched-chain, or cyclic hydrocarbon group containing one or more carbon—carbon double bonds and containing from 2 to about 18 carbon atoms. Any of the carbon atoms may be substituted with one or more substituents selected from alkoxy, acyloxy, acylamido, halogen, nitro, sulfhydryl, sulfide, carboxyl, oxo, seleno, phosphate, phosphonate, phosphine, and the like. Example of such alkenyl groups include ethenyl, propenyl, allyl, 1,4-butadienyl, 2-pentenyl, 3-pentenyl, 4-pentenyl, 2,6-decadienyl, 2-fluoropropenyl, 2-methoxypropenyl, 2-carboxypropenyl, 3-chlorobutadienyl, and the like.

As used herein, the term "cycloalkyl" or "cycloalkenyl," alone or in combination, means an alkyl or alkenyl group which contains from about 3 to about 12 carbon atoms and is cyclic. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Example of cycloalkyl groups include cyclopropyl, cyclobutyl, cyclopentyl, cyclohexyl, cycloheptyl, 2-methylcyclopentyl, 3-methylcyclohexyl, various substituted derivatives, and the like. Example of cycloalkenyl groups include cyclopentenyl, cyclohexenenyl, cycloheptenyl, and the like.

As used herein, the term "alkynyl," alone or in combination, means a straight-chain or branched-chain hydrocarbon group containing one or more carbon—carbon triple bonds and containing from 2 to about 18 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such alkenyl groups include ethynyl, propynyl, 1,4-butadiynyl, 3-pentynyl, 2,6-decadiynyl, 2fluoropropynyl, 3-methoxy-1-propynyl, 3-carboxy-2-propynyl, 3-chlorobutadiynyl, and the like.

As used herein, in the term "aryl," alone or in combination, means an optionally substituted carbocyclic aromatic system containing from 1 to 4 rings, wherein said rings may be attached in a pendant manner to each other or may be fused to each other. Examples of aryl groups include phenyl, naphthyl, bipehenyl, anthroacenyl, and the like. Suitable substituents include hydroxy, alkoxy, cycloallyl, alkyl, heterocyclic, thio, thioalkyl, fluro, chloro, bromo, iodo, carboxy, carboxyalkyl, carbamoyl, carbamide, amino, amidino, phosphate, phosphonate, phosphinate, phosphinyl, their derivatives, and the like.

As used herein, the term "heterocyclic," alone or in combination, means a saturated or unsaturated monocyclic or multi-cyclic group containing one or more heteroatoms selected from the group consisting of oxygen, nitrogen, sulfur, phosphorous, selenium, and silicon. Substituted heterocyclic means heterocyclic groups substituted on one or more carbon atoms with one or more substituents selected from the group consisting of hydroxy, alkoxy, thio, thioalkyl, fluro, chloro, bromo, iodo, carboxy, carboxyalkyl, carbomoyl, carbamide, amino, amidino, phosphate, phosphonate, phosphinate, phosphinyl, their derivatives, and the like.

Bilirubin analogs with certain geminal substitutions at the C10 position (i.e., at $R^1$ and $R^2$ in Formula (I)), for example gem-dimethyl or other tertiary carbocation substituted compounds (as described in, e.g., Xie, M. and Lightner, D. A. Tetrahedron 49:2185–2200 (1993), herein incorporated by reference), have been discovered to have similar susceptibility to diazo reagents as has bilirubin. This feature was unexpected, since substitutions at C10 would presumably increase the steric hindrance at the C9 and C11 positions to resist attack by the diazo reagent. These bilirubin analogs' resistance to oxidation while still being reactive with diazo compounds makes them good substitutes for natural bilirubin in calibration and control solutions such as those commonly used in clinical laboratories. "Bilirubin analog" "bilirubin derivative," or "bilirubin substitute" as used herein means a bilirubin-like compound, whether conjugated or unconjugated, synthetic or derived from natural bilirubin, having at least one dipyrrinone moiety and which is susceptible to diazotization.

The bilirubin analogs of the invention can be used as substitutes for bilirubin in any analytical use, whether research or clinical, where bilirubin is used or measured. Such uses can be as a control sample or calibrating reagent for total and direct bilirubin determinations in patient samples such as bilirubin in blood/serum or urobilinogen in urine.

The bilirubin analogs of the invention have superior stability, and are thus very useful in solutions requiring long shelf life. Liquid analytical solutions eliminate many varaiables commonly associated with lyophilized reagents, such as pepetting and mixing errors, short stability claims, and uncertain water quality. Additionally, they are ready to use from the bottle, eliminating pre-use preparation and waste. The bilirubin analogs disclosed herein are also stable when dry, and are often more soluble than natural bilirubin, making them advantageous for use in dried and/or lyophilized forms of calibrators and controls that are reconstructed prior to use (e.g., by adding water).

Methods of Using Compounds as Calibration and Control Reagents

The compositions of the invention are particularly useful as substitutes for natural bilirubin in analytical chemistry applications that rely on diazotization of bilirubin, but can be detected by any means that natural bilirubin can be detected. Commonly, it is desirable to quantitate bilirubin in clinical samples, and this is generally done by optical methods such as spectroscopy. The most common method for detection of bilirubin for clinical and research purposes is the diazo method, such as described by Malloy and Evelyn (*J. Biol. Chem.* 119:481–90, 1937), Dorimas et al. (*Clin. Chem.* 29:297–301, 1983), and Michaelsson (*Scand. J. Clin. Lab Inves.* 13 (Suppl.), 1–80, 1961), all herein incorporated by reference. The synthetic bilirubin analogs of the invention are diazotized essentially the same as natural bilirubin, and form colored products which can be measured spectrophotometrically. Diazotization reactions are preferred in clinical samples and in clinical calibration and control solutions because other common ingredients in such samples and solutions absorb in the same wavelength range as bilirubin. Most samples contain serum or urine proteins and metabolites, which can interfere with direct bilirubin detection. Conversion of bilirubin to a diazotized product makes identification and quantification of bilirubin easier by shifting the detection wavelength into a range not absorbed by multiple other sample or solution components (e.g., shifting absorbance from about 454 nm to about 600 nm).

Most control and calibration lyophilates and solutions are serum or urine based, although for purposes of the invention, the compound can be suspended in any liquid, preferably aqueous, that is compatible with the device or method of assay being used. For example, saline, water, urine or serum natrices, or any other solution may be used. Ordinarily, the base matrix of clinical control or calibration solutions or lyophilisates are formulated to mimic a physiological or body fluid, in order to adequately verify the functionality of the instrument and reagent used to diagnose patients. They are often derived from water, or human or animal fluids such as blood. Processing of such derivatives, such as serum, is targeted toward enhancing the performance and stability of the product. Such serum processing involves isolating plasma and removing the fibrin (clots). In addition, a host of specific processes can follow, including heat denaturation, lipid stripping, charcoal filtering, affinity chromatography, etc. The base matrices can have chemicals, drugs, proteins, preservatives, stabilizers, antioxidants, buffers, antimicrobials, protease inhibitors, or any desired analyte or other additives added to the control or calibration solution in addition to the synthetic bilirubin analogs of the invention. Such additives enhance performance, functionality, and stability.

Natural bilirubin is found in body in a "conjugated" or "direct" form, meaning that it has been conjugated with glucoronic acid in the liver to form bilirubin mono- or diglucuronide. Conjugated bilirubin reacts directly with diazo reagents (such as 3,5-dichlorophenyl; diazotized sulfanilate or other sulfanoic acids; 2,4-dichloropehenyldiazonium salt, 2-chloro-4-nitrophenyl diazonium salt and other halobensenediazonium salts: 2-methoxy-4-nitrophenyldiazonium tetraborate, 2-methoxy-5-(tetradecyloxycarbonyl) bensenediazonium tetrafluroborate, 2-ethyoxy-5-(hexadecyloxycarbonyl) benzenediazonium hexafluroborate, etc.), and is water soluble. "Unconjugated" or "indirect" bilirubin is an erthrocyte breakdown product which has not yet been conjugated with glucuronic acid and is associated with lipid. It reacts with diazo reagents only if a solubilizer or accelerator compound is added, such as a alcohol, sodium benzoate, or caffeine. Total bilirubin is the combined conjugated and unconjugated bilirubin in a sample. The bilirubin analog compounds of the invention exhibit the characteristics of natural bilirubin in that they have lipid and water soluble forms, and can be "conjugated" synthetically as desired by substitution of a appropriate groups.

The different reactivities of conjugated and unconjugated bilirubin make possible a distinction between them analytically, a feature useful in clinical diagnosis. For example, a clinical serum sample may have both conjugated and unconjugated bilirubin (in solution or bound to serum lipids, respectively). A first reaction product. A second reaction can then be done by adding a diazo reagent to the patient sample, allowing it to react with the conjugated bilirubin and spectrophotometrically measuring the reaction product. A second reaction can then be done (to the same or another aliquot of the sample) by adding the diazo reagent (if a new aliquot) and an accelerator to the sample, which reacts with both the conjugated (if a new aliquot) and an unconjugated bilirubin, giving a spectrophotometric reading of the total bilirubin in the sample. By substracting the total reading from the conjugated reading, a quantitative value for the unconjugated component can be deducted by comparing the reading to those taken from a control sample or samples with known concetrations of bilirubin or bilirubin analog, or by comparison to a calibration curve generated with one or more concentrations of bilirubin analog. A specific protocol is described by way of example in Example 1, below.

The bilirubin analogs of the invention are ideal for use in generating such control and calibration readings and curves. Because of the ready oxidation of natural bilirubin to biliverdin, control and calibration solutions using natural bilirubin suffer from inherent instability, even over a period of hours which can affect the accuracy of the readings generated. Therefore, it is advantageous to use bilirubin analogs susceptible to slow or no oxidation, and which, chemically and conformationally, can associate with lipids or be water soluble as can natural bilirubin.

The compositions and methods of the invention are also amendable to use in "dry chemistry" analytical methods, where diazo reagents on test strips are exposed to patient samples and liquid (reconstituted or supplied in liquid form) controls/calibrators.

Compositions

The compositions of the invention have the generic structure of Formula (I):

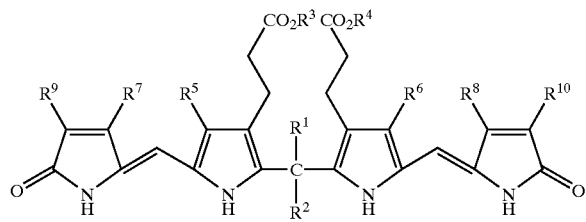

(I)

wherein $R^1$ and $R^2$ are each independently selected from alkyl, alkenyl, alkynyl, heterocyclic, and aryl;

$R^3$ and $R^4$ are independently selected from hydrogen, alkyl, alkenyl, and glucoronyl, and $R^5$, $R^6$, $R^7$, $R^8$, $R^9$ and $R^{10}$ are each independently selected from hydrogen, alkyl, tauryl, aryl, and alkenyl, with the proviso that when $R^3$ and $R^4$ are both hydrogen, at least one of $R^5$, $R^6$, $R^7$, $R^8$, $R^9$ and $R^{10}$ is not alkyl, preferably not alkyl or alkenyl.

Preferred compounds of the invention are those having the general structure of Formula (I) above, where $R^5$, $R^6$, $R^7$, $R^8$, $R^9$ and $R^{10}$ are not hydroxyl, amine, sulfate, nitrate, or other polar groups, since such groups may damage certain automated assay equipment and cause false readings. Alterations at these positions affect solubility properties of the compound, and it is desirable that these R groups are not particularly bulky. If a lipid soluble form, or unconjugated analog, of the molecule is desired, then $R^3$ and $R^4$ are preferably hydrogen. If a more water soluble form, or conjugated analog, is desired, $R^3$ and $R^4$ are preferably alkyl, tauryl, or glucuronyl groups.

Preferred compounds for use in the methods of the invention have methyl groups at $R^1$ and $R^2$ such as in Formula (II) below. In particularly preferred compounds of Formula (II), $R^5$, $R^6$, $R^7$, $R^8$, $R^9$ and $R^{10}$ are methyl groups, and $R^3$ and $R^4$ are hydrogen; or $R^5$, $R^6$, $R^7$, $R^8$, $R^9$ and $R^{10}$ are all ethyl groups.

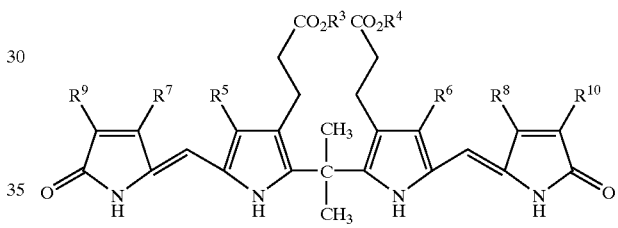

(II)

In other preferred compounds, $R^3$ and $R^4$ are selected independently from hydrogen, alkyl, tauryl, and glucoronyl. Another preferred compound is

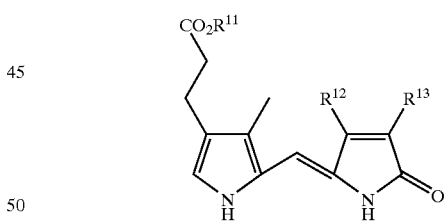

(III)

wherein $R^{11}$ is selected from the group containing hydrogen, alkyl, tauryl, and glucoronyl and $R^{12}$ and $R^{13}$ are independently selected from the alkyl group.

The following Example is intended to be illustrative and is not intended to limit the invention in any way.

EXAMPLE

Use of Calibration and Control Solutions in Bilirubin Assays

Determination of Total and Conjugated Bilirubin in Serum (Jendrassik and Grof Technique)

A morning serum or plasma sample from a fasting subject is preferably used as the specimen. Hemolysis should be avoided, since it produces falsely low values with diazo methods. Because both conjugated bilirubin are photooxidized when exposed to white or ultraviolet light, specimens should be protected from direct exposure to either artificial light or sunlight as soon as they are drawn. The sensitivity to light is temperature-dependent; for optimal stability, store specimens in the dark and at low temperatures.

Total bilirubin in serum or plasma is measured by adding caffeine reagent (below) as the accelerator to the specimen followed by the addition of diazotized sulfanilic acid. During the incubation period, both conjugated and unconjugated bilirubin react with the diazo reagent to produce azobilirubin. Ten minutes after diazotized sulfanilic acid is added, solutions of ascorbic acid, alkaline tartrate, and dilute hydrochloric acid are added to the reaction mixture. The absorbance of the resulting blue-green azobilirubin solution is measured at 600 nm.

To measure conjugated bilirubin, the serum or plasma is acidified with dilute hydrochloric acid and then mixed with diazotized sulfanilic acid to produce azobilirubin. Only conjugated bilirubin reacts with the diazo reagent in the absence of the accelerator. The reaction is stopped by the addition of an ascorbic acid solution. Then, an alkaline tartrate solution is added to the reaction mixture, followed by addition of the caffeine reagent. The latter shifts the absorbance peak of azobilirubin from 585 to 600 nm; the absorbance is measured at 600 nm. The tartrate reagent provides an alkaline pH to produce the blue and more intense color of azobilirubin.

Reagents
1. Caffeine-benzoate reagent. Dissolve 56 g anhydrous sodium acetate, 56 g sodium benzoate, 1 g disodium ethylenediaminetetraacetic acid (EDTA), and 37 g caffeine in ~700 mL of reagent-grade water. Dilute to exactly 1 L. This reagent is stable for at least 6 mo at room temperature.
2. Hydrochloric acid, 0.05 mol/L.
3. Sulfanilic acid, 5 g/L. Add 5 g of sulfanilic acid to 700 mL of reagent-grade water. Add 15mL of concentrated hydrochloric acid. Dilute to 1 L. Store at room temperature.
4. Sodium nitrite, 5 g/L: Dissolve 0.5 g of sodium nitrite in 70 mL of reagent-grade water and dilute to 100 mL. Store at 4° C. Prepare fresh every 2 weeks.
5. Diazotized sulfanilic acid. Mix 20 mL of the stock sulfanilic acid solution (Reagent No. 3) with 0.5 mL of a stock solution of sodium nitrite (Reagent No. 4). Prepare fresh daily and store at 4° C.
6. Ascorbic acid solution, 40 g/L. Dissolve 200 mg of ascorbic acid in 5 mL of water. Prepare fresh daily and store at 4° C.
7. Alkaline tartrate solution. Dissolve 75 g of sodium hydroxide and 320 g of sodium potassium tartrate in 700 mL of reagent-grade water. After the solution has cooled, dilute to exactly 1 L. This reagent is stable for at least 6 mo at room temperature.
8. Tris buffer (0.1 mol/L pH 7.4). Dissolve 12.1 g of tris(hydroxymethyl)aminomethane in 800 mL reagent-grade water. Adjust to pH 7.4 ±0.05 with hydrogen chloride and dilute to exactly 1 L. Store at 4° C. Solution is stable for at least 6 mo.
9. Bovine serum albumin (BSA) diluent (40 g/L). Add 8.0 g of BSA to 200 mL of tris buffer. Store at 4° C. if used within 1 wk; store at less than −20° C. if not used within 1 wk.
10. Sodium carbonate (0.1 mol/L). Dissolve 0.12 g of $Na_2CO_3 \cdot 1\, H_2O$ in 10 mL of water.

Calibrators and Calibration

Bilirubin analogs such as Formula (II) above are used for establishing calibration curves. Bilirubin analogs used to prepare calibrators should have an extinction coefficient at 453 nm of 60,700 ±1600 $(L)(mol^{-1})(cm^{-1})$ in chloroform at 25° C. Pure bilirubin, after diazotization, has a molar absorptivity at 600 nm of 75,080±1520 $(L)(mol^{-1})(cm^{-1})$, and the diazotized bilirubin analog selected should exhibit similar characteristics unless validated in another way. An acceptable diluent for unconjugated bilirubin analog is BSA Cohn Fraction V, 40 g/L. Bilirubin calibrators to be used for the preparation of the calibration curve is prepared as follows:

1. Stock Calibrator (20 mg/dL). Weigh 20.0 mg of bilirubin analog and transfer to a 100-mL volumetric flask; dissolve by adding 1.0 mL of dimethyl sulfoxide and 2.0 mL of sodium carbonate solution (Reagent No. 10). When transferring the analog to the 100-mL volumetric flask, use the dimethyl sulfoxide for quantitative transfer of any bilirubin that sticks to the weighing dish. Dilute the solution to 100 mL with the BSA diluent (Reagent No. 9).
2. Working Calibrators. These solutions are used for the generation of a calibration curve and are prepared from the stock calibrator and Reagent No. 9 as follows:

| Total Bilirubin Analog (mg/dL) | 40 g/L BSA (mL) | Stock Calibrator (mL) |
| --- | --- | --- |
| 0 | 4.0 | 0 |
| 2 | 9.0 | 1.0 |
| 5 | 3.0 | 1.0 |
| 10 | 2.0 | 2.0 |
| 15 | 1.0 | 3.0 |
| 20 | 0 | 4.0 |

3. Prepare a calibration curve by determining the absorbance values of azobilirubin-analog produced by each of the calibrating solutions. The calibration curve is then used as quantitation in the analysis of serum bilirubin. The relationship between absorbance and bilirubin (analog) concentration should be linear up to 20 mg/dL.

Procedure

Total Bilirubin
1. Add 2.0 mL of caffeine reagent (Reagent No. 1) to a glass test tube labeled "T" (total).
2. Add 0.2 mL of specimen to the test tube.
3. Add 0.5 mL of freshly prepared diazotized sulfanilic acid reagent (Reagent No. 5) to the test tube and mix.
4. Exactly 10 min after the addition of diazotized sulfanilic acid, add, in succession, 0.1 mL of ascorbic acid solution, 1.5 mL of alkaline tartrate, and 1.0 mL of hydrochloric acid, 0.05 mol/L (Reagents Nos. 6, 7, and 2) to the test tube and mix.
5. Read the absorbance of the solution in tube T at 600 nm against that of tube B (from step 5 in the conjugated bilirubin method) set at zero absorbance.
6. Use the calibration curve to determine the concentration of total bilirubin in each unknown.

Conjugated Bilirubin
1. Add 1.0 mL of hydrochloric acid, 0.05 mol/L, (Reagent No. 2) to each of two glass test tubes, one labeled "C" (conjugated) and the other "B" (blank). Add 2.0 mL of caffeine-benzoate reagent to test tube B only.
2. Add 0.2 mL of specimen to each tube.
3. Add 0.5 mL of sulfanilic acid solution (Reagent No. 3) to tube B only and mix.
4. Add 0.5 mL of freshly prepared diazotized sulfanilic acid reagent (Reagent No. 5) to tube C and mix.

5. Exactly 10 min later, add 0.1 mL of ascorbic acid solution (Reagent No. 6) to test tubes B and C followed immediately by the addition of 1.5 mL of alkaline tartrate solution (Reagent No. 7) to test tubes B and C and mix.
6. Add 2.0 mL of caffeine reagent (Reagent No. 1) to test tube C and mix.
7. Read the absorbance of test tube C at 600 nm against that of test tube B set at zero absorbance.
8. Use the calibration curve to determine the concentration of conjugated bilirubin in each unknown.

The preceding description has been presented with reference to presently preferred embodiments of the invention. Workers skilled in the art and technology to which this invention pertains will appreciate that alterations and changes in the described methods may be practiced without meaningfully departing from the principles, spirit and scope of this invention.

Accordingly, the foregoing description should not be read as pertaining only to the precise methods described, but rather should be read consistent with and as support to the following claims which are to have their fullest and fair scope.

What is claimed is:

1. A method of quantifying bilirubin in a sample comprising:
    detecting bilirubin in a sample to obtain a first measurement indicative of the amount of bilirubin in the sample;
    detecting a known quantity of a compound of Formula (I):

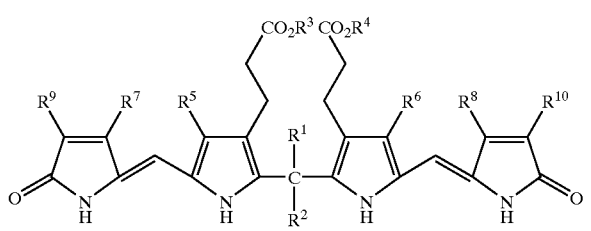

(I)

wherein:
    $R^1$ and $R^2$ are each independently selected from alkyl, alkenyl, alkynyl, heterocyclic, and aryl,
    $R^3$ and $R^4$ are independently selected from hydrogen, alkyl, alkenyl, taurine, tauryl, aryl, and glucoronyl, and
    $R^5$, $R^6$, $R^7$, $R^8$, $R^9$ and $R^{10}$ are each independently selected from hydrogen, alkyl, and alkenyl, in at least one control reagent to obtain a second measurement indicative of the amount of the compound of Formula (I) in the control reagent; and
    comparing the measurements to determine the amount of bilirubin in the sample relative to the amount of the compound of Formula (I) in the control reagent.

2. The method of claim 1 wherein the detecting comprises:
    contacting the bilirubin in the sample and the compound in the control reagent with a diazonium ion source to form a colored product; and
    measuring the colored product.

3. The method of claim 2 wherein the colored product is measured spectrophotometrically.

4. The method of claim 2 wherein the diazonium ion source is selected from the group consisting of:
    Diazotized sulfanilic acid;
    3,5-dichlorophenyldiazonium ion;
    2,5-dichlorophenyldiazonium ion;
    2-methoxy-4-nitrophenyldiazonium ion;
    2,4-dichlorophenyl diazonium ion;
    2-chloro-4-nitrophenyl diazonium ion;
    2-methoxy-5-(tetradecyloxycarbonyl) benzenediazonium ion; and
    2-ethyoxy-5-(hexadecyloxycarbonyl) benzenediazonium ion.

5. The method of claim 1 wherein the control reagent is in the form of a liquid.

6. The method of claim 1 wherein the control reagent is supplied in a dried form, the method further comprising reconstituting the dried control reagent with an aqueous solution prior to measuring the compound of Formula (I) in the control reagent.

7. The method of claim 1 wherein $R^1$ and $R^2$ are methyl.

8. The method of claim 7 wherein $R^5$, $R^6$, $R^7$, $R^8$, $R^9$ and $R^{10}$ are each independently selected from methyl, ethyl, and propyl.

9. The method of claim 8 wherein $R^5$, $R^6$, $R^7$, $R^8$, $R^9$ and $R^{10}$ are each ethyl.

10. The method of claim 9 wherein $R^3$ and $R^4$ are each hydrogen.

11. A method of calibrating a device to accurately detect bilirubin comprising:
    providing in a calibration reagent a known quantity of a compound of Formula (I):

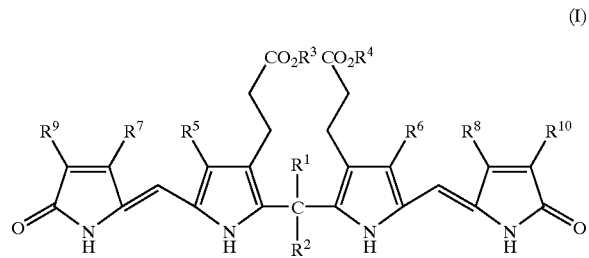

(I)

wherein:
    $R^1$ and $R^2$ are each independently selected from alkyl, alkenyl, alkynyl, heterocyclic, and aryl,
    $R^3$ and $R^4$ are independently selected from hydrogen, alkyl, alkenyl, aryl, tauryl, and glucoronyl, and
    $R^5$, $R^6$, $R^7$, $R^8$, $R^9$, $R^{10}$ are each independently selected from hydrogen, alkyl, and alkenyl;
    determining a first value that corresponds to the known quantity of the compound of Formula (I) in the calibration reagent;
    measuring the calibration reagent in a device to obtain a second value;
    adjusting the device such that a subsequent measuring of the calibration reagent would yield a measurement wherein the second value is equal to the first value.

12. The method of claim 11 wherein the measuring comprises:
    contacting the compound of Formula (I) in the calibration reagent with a diazonium ion source to form a colored product; and
    measuring the colored product.

13. The method of claim 12 wherein the colored product is measured spectrophotometrically.

14. The method of claim 12 wherein the diazonium ion source is selected from the group consisting of:
Diazotized sulfanilic acid;
3,5-dichlorophenyldiazonium ion;
2,5-dichlorophenyldiazonium ion;
2-methoxy-4-nitrophenyldiazonium ion;
2,4-dichlorophenyl diazonium ion;
2-chloro-4-nitrophenyl diazonium ion;
2-methoxy-5-(tetradecyloxycarbonyl) benzenediazonium ion; and
2-ethyoxy-5-(hexadecyloxycarbonyl) benzenediazonium ion.

15. The method of claim 11 wherein the calibration reagent is in the form of a liquid.

16. The method of claim 11 wherein the calibration reagent is supplied in a dried form, the method further comprising reconstituting the dried calibration reagent with an aqueous solution prior to measuring the compound of Formula (I) in the calibration reagent.

17. The method of claim 11 wherein $R^1$ and $R^2$ are methyl.

18. The method of claim 17 wherein $R^5$, $R^6$, $R^7$, $R^8$, $R^9$ and $R^{10}$ are each independently selected from methyl, ethyl, and propyl.

19. The method of claim 18 wherein $R^5$, $R^6$, $R^7$, $R^8$, $R^9$, and $R^{10}$ are each ethyl.

20. The method of claim 19 wherein $R^3$ and $R^4$ are each hydrogen.

21. The method of claim 11 wherein at least two calibration reagents containing different concentrations of the compound of Formula (I) are used to make a standard curve.

22. A composition for use as a calibration or control reagent comprising a synthetic bilirubin analog of Formula (I):

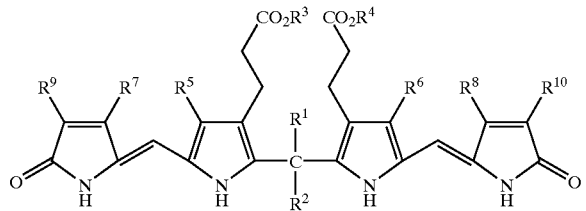

(I)

wherein:
$R^1$ and $R^2$ are each independently selected from alkyl, alkenyl, alkynyl, heterocyclic, and aryl,
$R^3$ and $R^4$ are independently selected from hydrogen, alkyl, alkenyl, tauryl, aryl, and glucoronyl, and
$R^5$, $R^6$, $R^7$, $R^8$, $R^9$ and $R^{10}$ are each independently selected from hydrogen, alkyl, and alkenyl, with the proviso that when $R^3$ and $R^4$ are both hydrogen, at least one of $R^5$, $R^6$, $R^7$, $R^8$, $R^9$ and $R^{10}$ is not alkyl.

23. The composition of claim 22 further comprising an aqueous liquid.

24. The composition of claim 23 further comprising processed serum or urine.

25. The composition of claim 22 further comprising processed serum.

26. The composition of claim 25 wherein said serum is of human or bovine origin.

27. The composition of claim 22 further comprising processed urine.

28. The composition of claim 22 further comprising at least one additional ingredient selected from the group consisting of a preservative, an antibiotic, and a drug.

29. The composition of claim 22 wherein the composition has a concentration of water of less than 1% by volume.

30. The composition of claim 29 wherein the composition is in lyophilized form.

31. The composition of claim 30 wherein further when $R^3$ and $R^4$ are both hydrogen, at least one of $R^5$, $R^6$, $R^7$, $R^8$, $R^9$ and $R^{10}$ is not alkenyl.

32. A composition for use as a calibration or control reagent comprising:
a bilirubin analog of Formula (II):

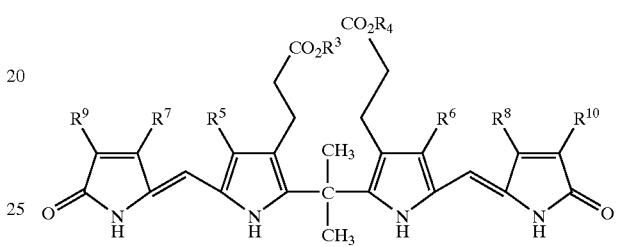

(II)

wherein $R^3$ and $R^4$ are selected independently from the group containing hydrogen, alkyl, tauryl, aryl, and glucoronyl, $R^5$, $R^6$, $R^7$, $R^8$, $R^9$ and $R^{10}$ are each independently selected from hydrogen, alkyl, and alkenyl; and
one additional component selected from processed serum and processed urine.

33. The composition of claim 32 in the form of a liquid.

34. The composition of claim 32 further comprising at least one of a preservative, an antibiotic, a drug of abuse and a therapeutic drug.

35. The composition of claim 32 wherein $R^7$, $R^8$, $R^9$ and $R^{10}$ are each ethyl.

36. A composition for use as a calibration or control reagent comprising:
a bilirubin analog of Formula (III):

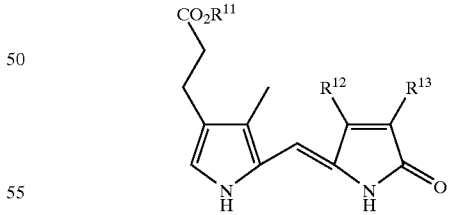

(III)

wherein $R^{11}$ is selected from the group containing hydrogen, alkyl, tauryl, aryl, and glucoronyl, and $R^{12}$ and $R^{13}$ are an alkyl group, and
one of processed serum and processed urine.

* * * * *